(12) United States Patent
Middelbeek et al.

(10) Patent No.: US 9,119,794 B2
(45) Date of Patent: Sep. 1, 2015

(54) PROCESS TO FORM A TABLET AND APPARATUS SUITABLE FOR APPLYING THIS PROCESS

(75) Inventors: Hans Almer Middelbeek, Oss (NL); Jozefus A. C. Smit, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 435 days.

(21) Appl. No.: 13/266,510

(22) PCT Filed: Apr. 28, 2010

(86) PCT No.: PCT/EP2010/055679
§ 371 (c)(1),
(2), (4) Date: Oct. 27, 2011

(87) PCT Pub. No.: WO2010/125084
PCT Pub. Date: Nov. 4, 2010

(65) Prior Publication Data
US 2012/0049412 A1 Mar. 1, 2012

Related U.S. Application Data

(60) Provisional application No. 61/173,631, filed on Apr. 29, 2009.

(30) Foreign Application Priority Data

Apr. 29, 2009 (EP) ..................................... 09159040

(51) Int. Cl.
*B29C 39/38* (2006.01)
*B65D 85/00* (2006.01)
(Continued)

(52) U.S. Cl.
CPC ................. *A61K 9/2095* (2013.01); *A61J 3/10* (2013.01); *A61J 7/0007* (2013.01); *A61K 9/0056* (2013.01)

(58) Field of Classification Search
CPC ... A61K 9/2095; A61K 9/0056; A61J 7/0007; A61J 3/10
USPC ............................. 264/299; 425/357; 206/438
See application file for complete search history.

(56) References Cited

U.S. PATENT DOCUMENTS 2,552,027 A 5/1951 Bird et al,
5,382,437 A 1/1995 Ecanow
(Continued)

FOREIGN PATENT DOCUMENTS

EP 0 450 141 5/1995
EP 1 165 053 3/2004
(Continued)

OTHER PUBLICATIONS

Chandrasekhar, Rahul et al. "The Role of Formulation Excipients in the Development of Lyophilised Fast-Disintegrating Tablets", European Journal of Pharmaceutics and Biopharmaceutics (2009) 72:119-129.
(Continued)

*Primary Examiner* — Alison Hindenlang
*Assistant Examiner* — Robert J Grun

(57) ABSTRACT

The present invention pertains to a process for the preparation of a fast-disintegrating tablet (30) containing a medicinal substance, comprising the steps of providing a fluid formulation comprising the medicinal substance, providing a solid element (100) having formed therein at least one cavity, (101) cooling the solid element (100) to a temperature below a freezing temperature of the formulation, filling the cavity with the fluid formulation, solidifying the formulation while present in the cavity (101) to form a solid pellet comprising the medicinal substance without actively shaping the entire surface of the pellet, taking the pellet out of the cavity and drying the pellet in a vacuum to obtain the tablet. The invention also pertains to a system for performing such a process and a package containing the resulting tablet.

12 Claims, 7 Drawing Sheets

Figure 1A:
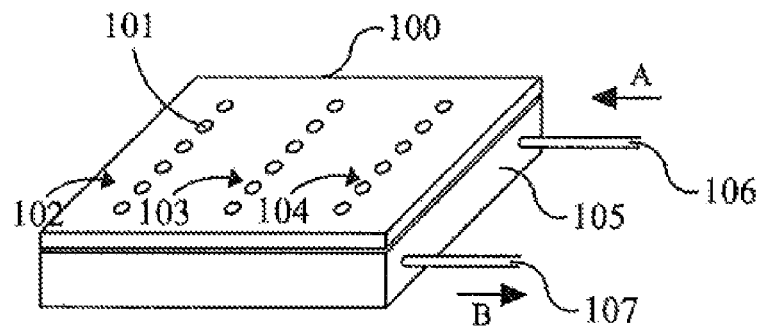

(51) Int. Cl.
*B28B 7/42* (2006.01)
*A61K 9/20* (2006.01)
*A61J 3/10* (2006.01)
*A61J 7/00* (2006.01)
*A61K 9/00* (2006.01)

(56) References Cited

U.S. PATENT DOCUMENTS

| | | | |
|---|---|---|---|
| 5,384,124 | A | 1/1995 | Courteille et al. |
| 6,177,104 | B1 | 1/2001 | Allen et al. |
| 6,224,905 | B1* | 5/2001 | Lawrence et al. ............. 424/464 |
| 6,471,758 | B1 | 10/2002 | Kelderman et al. |
| 2006/0057207 | A1 | 3/2006 | Ziegler et al. |
| 2010/0301519 | A1* | 12/2010 | Odagi et al. ................. 264/310 |

FOREIGN PATENT DOCUMENTS

| | | |
|---|---|---|
| FR | 2 868 520 | 10/2005 |
| WO | WO 93/12770 | 7/1993 |
| WO | WO 97/48383 | 12/1997 |
| WO | WO 03/028619 | 4/2003 |
| WO | 03/094886 A2 | 11/2003 |
| WO | WO 2006/094974 | 9/2006 |

OTHER PUBLICATIONS

Dobetti, Luca "Fast-Melting Tablets: Developments and Technologies", Pharmaceutical Technology Drug Delivery (2001) pp. 44-50.

Kaushik, Deepak et al. "Orally Disintegrating Tablets: An Overview of Melt-Mouth Tablet Technologies and Techniques", Tablets and Capsules (Jul. 30, 2004).

International Search Report corresponding to PCT/EP2010/055679, mailed Aug. 3, 2010.

Chandrasekhar, et al., "The role of formulation excipients in the development of lyophilised fast-disintegrating tablets," European Journal of Pharmaceuticals and Biopharmaceuticals, vol. 72, 2009, pp. 119-129.

Dobetti, et al., "Fast-Melting Tablets: Developments and Technologies," Pharmaceutical Technology, Drug Delivery, 2001, pp. 44-50.

Kaushik, et al., "Orally Disintegrating Tablets: An Overview of Melt-in-Mouth Tablet Technologies and Techniques," Jul. 30, 2004.

* cited by examiner

PROCESS TO FORM A TABLET AND APPARATUS SUITABLE FOR APPLYING THIS PROCESS

CROSS-REFERENCE TO RELATED APPLICATIONS

This application is a national stage entry under 35 U.S.C. 371 of PCT/EP2010/055679, filed on Apr. 28, 2010, which claims priority to U.S. Provisional Application No. 61/173,631, filed on Apr. 29, 2009, and EP Application No. 09159040.6, filed on Apr. 29, 2009. The content of PCT/EP2010/055679 is hereby incorporated by reference in its entirety.

GENERAL FIELD OF THE INVENTION

The present invention pertains to a process for the preparation of a fast-disintegrating tablet containing a medicinal substance.

BACKGROUND OF THE INVENTION

A process for the preparation of fast-disintegrating tablets (in this specification also denoted as "disintegrating tablets") is known i.a. from U.S. Pat. No. 5,384,124 assigned to Farmalyoc. In the known process a paste comprising one or more medicinal substances is formed, which paste is mechanically divided into unitary doses having a well defined shape and volume, by distributing the paste in cavities of predetermined shape and size, which cavities are present in a polyvinyl chloride carrier element. After distributing the paste, the carrier element is put in a lyophiliser and the paste is freeze-dried. This way, each unitary dose is formed into a tablet. The advantage of the freeze-drying process is not only that the medicinal substance is brought in a very stable form, but also that a solid dosage form is obtained that disintegrates upon contact with a liquid. In particularly, if the paste originally was based on water as the carrying solvent (the term "solvent" includes any liquid medium may serve as a carrier for other substances), such a tablet will normally disintegrate upon contact with water. Such a dosage form is for example particularly suitable for tablets that have to disintegrate fast when taken orally (e.g. tablets containing medicinal substances that lose their activity when passing the gastric channel), or for tablets that are used to in situ constitute a medicine for oral or parenteral administration (i.e. at the site of administration, immediately preceding the actual administration).

A variety of medicinal substances and/or combinations thereof can be used as the active ingredient in a fast disintegrating tablet, such as for example analgesics and anti-inflammatory agents, antacids, anthelmintics, anti-arrhythmic agents, anti-bacterial agents, anti-coagulants, anti-depressants, anti-diabetics, anti-diarrheals, anti-epileptics, anti-fungal agents, anti-gout agents, anti-histamines, anti-hypertensive agents, anti-malarials, anti-migraine agents, anti-muscarinic agents, anti-neoplastic agents and immunosurpressants, anti-psychotics, anti-protozoal agents, anti-rheumatics, anti-thyroid agents, anti-viral agents, anxiolytics, sedatives, hypnotics and neuroleptics, beta-blockers, cardiac inotropic agents, corticosteroids, cough suppressants, cytotoxics, decongestants, diuretics, enzymes, anti-parkinson agents, gastro-intestinal agents, histamine receptor antagonists, lipid regulating agents, local anaesthetics, neuromuscular agents, nitrates and anti-anginal agents, opioid analgesics, proteins, peptides, recombinant drugs, sex hormones, contraceptives, spermicides, stimulants etc.

The known method is being widely used in the life-sciences industry (see for example "Orally disintegrating tablets: an overview of melt-mouth tablet technologies and techniques" by Deepak Kaushik, Harish Dureja and T. R. Saini, Maharishi Dayanand University and Shri G. S. Institute of Technology and Science, as published in "Tablets and Capsules", 30 Jul. 2004). In particular technologies such as Zydis (Catalent Pharma Solutions, Somerset, N.J., USA) and Lyoc (Laboratoires Farmalyoc, Maisons-Alfort, France) use this known process. Typically the starting paste or fluid formulation is prepared and dosed into a preformed blister pack. This pack, i.e. the material present in the pack, is then frozen and subjected to freeze-drying to remove water. The resultant structures are inherently very porous and rapidly disintegrate when they contact saliva.

Indeed, the known method is very advantageous in that tablets can be made that very rapidly disintegrate (which tablets are also known as Fast-Melting Tablets, or FMT's), show improved pharmacokinetic characteristics when compared with reference oral solid formulations, increased bioavailability, show improved patient compliance and side-effect reduction (see "Fast-Melting Tablets: Developments and Technologies" by Luca Dobetti, in Pharmaceutical Technology Drug Delivery, 2001, pp 44-50). Known disadvantages are that the tablets have a relatively poor mechanical stability and high cost of production. These disadvantages however are believed to be inherent due to the freeze-dry process used: Freeze-drying needs expensive equipment and inherently leads to mechanically less stable tablets when compared e.g. to traditional compression techniques. Due to this fact, the known process takes place by using the final tablet package (i.e. the blister package) as a carrier throughout the complete process. This inherently means that each production step has to be adjusted such that it can be used in conjunction with this particular package. This limits the freedom of operation in the various manufacturing steps and thus increases cost price even further. However, given the advantages of freeze-dried products as disintegrating tablets, the inherent high cost price of the manufacturing process is accepted by the manufacturing practitioner.

It is noted that other methods to arrive at fast-disintegrating tablets are known from the prior art. For example, WO 93/12770 and US 2006/0057207 (both assigned to Pfizer Inc.) describe a method wherein the tablets are actively shaped over substantially their entire surface by compressing the frozen pellets in a closed mould. This known method thus defers from passively obtaining a tablet shape, for example by using a passively arrived shape that occurs through the mere action of gravity and surface tension. This way a predetermined shape can be arrived at easily in a controlled manner. This method however is disadvantageous in that it requires a rather complex die-and-punch assembly that is prone to leakage of the fluid formulation from the cavity (i.e. the closed mould). Also, frozen pellets tend to stick to either the die or punch due to the use of compression forces. An advantage indeed is that by compressing the frozen pellet, good mechanical properties are obtained which allow the frozen pellet to be taken out of the cavity integrally.

From WO 97/48383, U.S. Pat. No. 5,382,437 and EP 0 450 141 other methods are known wherein the fluid formulation is brought over into open cavities of a solid element which is at room temperature, whereafter this element is brought over in a freezer, typically for 30-60 minutes. This appears to be advantageous since the fluid formulation namely will nicely fill the cavity, thus leading to a frozen pellet of a size and shape that exactly corresponds to the size and shape of the cavity, and thus leading to a predictable pellet form. Disadvantages however are that a cooling-heating cycle has to take place with this method and also that the entire process is relatively slow. Also, there is a risk of loosing fluid from the cavity upon filling them with the (low viscosity) fluid formulation.

SUMMARY OF THE INVENTION

It is an object of the present invention to arrive at a process for obtaining a fast-disintegrating tablet using freeze-drying as a basic technology, which has a significantly reduced cost price per tablet, while at the same time having excellent disintegration properties. To this end a process according to the General Field Of The Invention as mentioned here-above has been devised comprising the steps of providing a fluid formulation comprising the medicinal substance, providing a solid element having formed therein at least one cavity, cooling the solid element to a temperature below a freezing temperature of the formulation, filling the cavity with the fluid formulation, solidifying the formulation while present in the cavity to form a solid pellet comprising the medicinal substance without actively shaping the entire surface of the pellet, taking the pellet out of the cavity, and drying the pellet in a vacuum to obtain the tablet. Applicant surprisingly found that the advantages of the known method can be preserved, while at the same time significantly increasing the freedom in the manufacturing process, and thus enabling a significant decrease the cost price per tablet, by firstly filling an open cavity with a fluid formulation comprising the medicinal substance (which also covers filling the cavity with two or more separate sub-formulations which together form the fluid formulation containing the medicinal substance) and then freezing the fluid formulation in that cavity to form a solid pellet by simply leaving the fluid formulation in the pre-cooled cavity, not applying any active shaping tools such that one may end up with an uncompressed frozen pellet having a shape (at the open end of the cavity) that is formed merely by gravitational forces and surface tension (a meniscus), taking the frozen pellet out of the cavity, and after that drying the pellet (for example in a lyophilising apparatus). It was also found that it is particularly advantageous to have the solid element at a temperature below the freezing temperature of the formulation upon filling the cavity. At first glance this seems a disadvantage: The fluid formulation namely will start to solidify immediately upon contact with the cavity wall, theoretically leading to a frozen pellet of a size and shape that does not correspond to the size and shape of the cavity, thus leading to an uncontrolled freezing process and thus an unpredictable pellet form. However, applicant found that for a temperature below the freezing temperature of the fluid formulation a filling speed can be found that is fast enough to counterbalance the immediate freezing of the fluid, simply because the amount of heat present in the flow of fluid formulation may simply counterbalance the extraction of heat by the cold solid element, or at least an adequate part of the heat extraction. Overall, the new process is easier to control: the temperature of the solid element can be kept at the same level, whereas a cooling-heating cycle has to take place with prior art methods. Moreover, the process is faster. Heat is already being extracted upon filling the cavity. Also, there is less risk of loosing fluid from the cavity, since the fluid will cool down very fast after entry of the cavity and thus will immediately show an increased viscosity.

In this new process the final tablet package does not need to be involved in any of the process steps. Therefore, not only a standard cheap package may be used, but also, each of the manufacturing steps can take place with tools optimised for their task. With the prior art process for example, where a blister package is used as the carrier for the tablets in a lyophiliser, the drying circumstances have to be adjusted to the relatively low amount of heat that can be transferred through the (plastic) package. This may significantly increase the thermal load (for example a high local temperature) on each tablet during the drying step and also may significantly increase the necessary process time.

Another major advantage of the present method is that the tablets in the finished packed product are not present in the mould in which they have been formed. With the prior art method as known from i.a. U.S. Pat. No. 5,384,124 the pellets are formed in the blister package which serves as a mould. The pellets however stay in their moulds during the complete process, until they are transformed into tablets present in their finished packaging. Therefore there is a high risk that the tablets more or less stick to the blister wall and can only be removed by applying considerable mechanical forces. This, in combination with the fact that freeze-dried tablets are inherently not too stable (when compared to classic compressed tablets) often results in tablets being broken even before they can be administered. This may lead to tablets not being used or too little active ingredient being administered to a patient.

Another important advantage of the present process is that the freezing step does not need to take place in the lyophiliser itself. In the process known from U.S. Pat. No. 5,384,124 the freezing step takes place in the lyophiliser since the paste is present in the blister package anyway. However, in the known process, extracting heat from the paste to freeze it takes a relatively long time. In the present method, by solidifying the fluid formulation in a separate step in a dedicated cavity, and thereafter taking the frozen pellet out of the cavity and subject it to a lyophilising action in an additional step, the initial freezing can be done significantly more efficiently.

Yet another substantial advantage of the present invention is that the step of obtaining the solid frozen pellets does not depend on the available drying capacity. Since the provision of the frozen pellets is completely independent of the drying step, the pellets can be produced separately and for example stored until drying capacity comes available. In particular when the medicinal substance is of biological origin, it is important that a batch of fluid formulation containing this substance can be completely processed into frozen pellets, independently from the currently available drying capacity.

With regard to the die-and-punch methods as known from the prior art, the present method has the important advantage that it does not suffer from leakage of the fluid formulation from the cavity. Since the fluid formulation is simply left to freeze in the open cavity without actively shaping the entire surface of the pellet by applying e.g. compression forces or other active moulding techniques that shape the surface of the pellet, there is no risk of fluid formulation being pressed out of the cavity. Also, there is a significantly decreased risk of the pellet sticking to any of the parts used for actively shaping the pellet. Surprisingly it appeared that by simply leaving the fluid formulation to freeze, without applying any compression forces, the pellet still may have sufficient mechanical strength to be taken out of the cavity for further processing such as lyophilising.

The present invention is based on several recognitions, the first one being that the finished freeze-dried product may be mechanically not too stable, but the intermediate frozen product surprisingly does not suffer from this disadvantage despite the fact that this frozen product is not compressed. This opens possibilities for additional mechanical handling of the intermediate pellet. However, such handling in the known Farmalyoc process makes no sense, since the frozen pellet is already present in the lyophiliser in its final blister package. Applicant however came to a second insight, namely that the drying step in this known process is very inefficient mainly due to the fact that when using the final tablet package as a carrier in the lyophiliser, the drying space is not adequately used (each tablet takes a relatively large amount of space since the tablets cannot be in a contiguous relation in the package). This inefficient use of the lyophiliser in the known process is inherent, but can be overcome by separating the freezing and drying step by using a carrier for the freezing step that differs from the carrier used in the drying step.

It is noted that the present invention also pertains to a system for performing a process as described here-above, comprising an element provided with multiple cavities, a filling unit for filling each cavity with a fluid formulation comprising a medicinal substance, a cooling unit for cooling the element below a freezing temperature of the formulation such that a solid pellet comprising the medicinal substance can be formed in each cavity upon freezing of the fluid formulation, a pushing element for pushing the pellets out of their respective cavity, and a chamber for drying the pellets in a vacuum to form tablets that disintegrate upon contact with a liquid.

The invention also pertains to a package (i.e. an air and water-tight packed product which can be used for commercial activities such a sales to an end-user) comprising a container having therein at least one fast-disintegrating tablet containing a medicinal substance, wherein the tablet is formed in a cavity using a method according to the present invention, the cavity being different from the container in which the tablet is packed. As described here-above, a major advantage of the present invention is that tablets in the finished packed product are not present in the mould in which they have been formed, which almost excludes the chance of a tablet sticking to its blister in the finished package. This near exclusion improves the convenience of handling the tablets by a physician, DVM, patient or the like. The container can for example be a cup with a lid, a vial, a syringe, a blister with a peel-off or push-through strip etc.

DEFINITIONS

A tablet is a solid dosage form, for example for direct oral, rectal or parenteral administration or for indirect administration for example after mixture with a carrier material, in particular a liquid, for administration in a dissolved or dispersed form. A tablet can be distinguished from powder or fine granules in that a tablet can be individually manually handled. A minimum length size of a tablet is 1 mm, preferably 2 mm, more preferably 4 mm and typically (but not necessarily) between 4 and 20 mm.

An orally disintegrating tablet is a freeze-dried tablet that disintegrates upon contact with saliva, for example in the oral cavity, within 60 seconds, preferably within 30 seconds, more preferably within 10 seconds.

Freeze-drying or lyophilisation is a process used in the creation of a stable preparation of a substance by freezing a fluid formulation containing the substance and substantially remove the frozen liquid under vacuum.

A vacuum is air or other gas at a reduced (sub-atmospheric) pressure.

To disintegrate is to lose unity and be reduced to fragments. The term "disintegrate" covers dissolution (having fragments at molecular level).

Fast-disintegration means disintegration which starts upon contact with a liquid, in particular water at 37° C., and is completed within 60 seconds, preferably within 30 seconds, more preferably within 10 seconds.

A medicinal substance is any substance that can be used to treat a disease or disorder, i.e. to aid in preventing, ameliorating or curing the disease or disorder. Such a substance may for example be a chemical or biological compound, such as a natural or synthetic peptide or protein, a (poly-)saccharide or any other organic or inorganic molecule, a dead or alive micro-organism, a dead or alive parasite etc.

A freezing temperature of a fluid formulation is a temperature at which the consistency of the formulation transforms from liquid to solid, i.e. a consistency which can withstand an external force without a change of form.

A heat conducting material is a material having a heat transfer coefficient of at least 1 W/mK (Watt per meter Kelvin).

Abhesive means the capability of resisting adhesion.

A crystalline material is a material that can form crystals upon solidification under equilibrium conditions.

A gelator is an agent that is capable of forming a network of molecules within a fluid to provide the fluid the consistency of a gel, i.e. having at least some self-supporting capacity (not being a free-flowing liquid under all circumstances). The term gelator also covers an agent comprising two or more different compounds or materials that each are capable of forming a network of molecules within a fluid.

EMBODIMENTS OF THE INVENTION

In an embodiment of the process according to the invention the formulation is cooled by extracting heat from the formulation through a cavity wall by conduction. This means that at least the main part (more than 50%) of the heat that is to be extracted to freeze the formulation, is extracted by conduction through the cavity wall. Preferably more than 80% up to virtually 100% of the heat is extracted by conduction through the cavity wall. In the known processes nearly all of the heat is extracted by convection, in particular using nitrogen gas that travels around the fluid formulation to extract heat until the formulation is solidified and has transformed into a frozen pellet. Although convection can be adequately used to freeze the fluid formulation, applicant found that when conduction is used, by having a heat conducting material around at least part of the fluid formulation, the cooling process may provide a pellet with advantageous mechanical stability, for example an adequate mechanical strength and/or low friability, while maintaining its fast disintegrating properties at an adequate level. The reason for this is not clear but may be due to the fact that extraction of heat by conduction provides a more efficient and thus significantly faster cooling process, which leads to a different arrangement of the constituting molecules in the pellet. It may very well be that a significantly faster cooling process leads to a solidification process that provides a more amorphous-like end-product, leading to a less vulnerable end-product. Because of the noted effect, a tablet obtained according to this embodiment of the present process is ideally suitable for an orally disintegrating tablet (for administration to humans or animals). Such a tablet ideally meets multiple demands, for example sufficient mechanical strength for manual handling (to enable easy removal of a tablet from a package and allow putting the tablet in the mouth of a patient), optionally possess mucoadhesive properties (for example such that a tablet will disintegrate in the mouth and not reach the stomach), while not being sticky in order not to hamper handling of the tablet, having an acceptable taste, and providing a very rapid disintegration (such that for example high blood levels of the medicinal substance can be obtained). The liquid formulation used for making the tablets may optionally contain additives such as for example surfactants or other substances which can be used to give the final tablet properties useful for the specific use of the tablet. Such substances may for example be colorants, sweeteners or other taste modifying or masking agents, preservatives, colouring agents, pH modifiers or any other substance that is compatible with the rest of the constituents of the tablet, and if necessary pharmaceutically acceptable for the intended patient.

It is noted that in the prior art methods, a small amount of heat may be extracted from the fluid formulation through the wall of the blister. This however does not qualify as heat extraction by conduction in the sense of the present invention since the blister package material is a plastic, which typically has a heat transfer coefficient of 0.1 to 0.2 W/mK, which inevitably means that the main part of the heat is extracted by other means than conduction (viz. convection).

In an embodiment, the volume of the pellet is larger than a maximum volume of a free droplet of the fluid formulation at a temperature and pressure used when filling the cavity. In this embodiment the pellet is bigger than a single free droplet of the fluid formulation. This embodiment is advantageous in obtaining tablets of a size that can be easily handled manually, based on a fluid formulation of which one single free droplet would only be as large as for example 50 µl. For example, if the fluid formulation is based on water as a solvent (carrier fluid) than a single free droplet at a temperature of 20° C. and a pressure of 1 atmosphere is about 50 µl. After freezing and drying such a droplet, the diameter will be about 2.3 mm. This is quite small for manual handling. It is preferred that larger tablets are made. In the prior art, this is accomplished by transforming the fluid formulation into a formulation such that droplets up to 1 ml can be obtained. For this however, all kinds of additives are required to give the fluid formulation a gel-like consistency. These additives not only make the production process more complex, they must also be taken into account when assessing compatibility with the subject patient, e.g. a human being or a pet. Although freezing one single droplet has advantages process wise, it was applicants merit to find out that constituting a pellet out of a volume that correspond to the volume of multiple single droplets, leads to less stringent conditions for the constituents of the fluid formulation, simply because less compounds need to be present in the formulation.

In a further embodiment, the speed at which the cavity is filled with the fluid formulation is chosen such that the surface of the part of the pellet that is in the cavity before the pellet is taken out of this cavity, is in essence a negative print of the surface of the cavity. It was found that a filling speed can be chosen such that the surface of the pellet, at least the part that is contiguous to the cavity, is in essence a negative print of the surface of the cavity (in essence meaning at least as far as visible with the naked human eye). When the filling speed is below this speed, an uneven pellet surface will be formed since the fluid that enters the cavity will solidify before it can completely wet the surface of the cavity. Complete wetting is found particularly suitable not only to form nice and smooth pellets and thus tablets, but also, this gives the opportunity to form a logo or any other identifying means in the tablet (for example a logo of the commercial party bringing the tablet to the market or any other imprint). For this, one needs to have a mirror image of the imprint in the cavity wall (either positive, that is being applied on top of the wall, or negative, that is being indented in the wall).

In another embodiment a cross-section of the part of the pellet that is in the cavity is smaller than a cross-section of the cavity at its entrance. In this embodiment the pellet can be easily removed from the cavity, for example by simply pushing or pulling the pellet out the cavity, using a mechanical force, air pressure, gravity etc.

In yet another embodiment the volume of the cavity is smaller than the volume of the pellet. In the prior art methods, a cavity is chosen that exactly corresponds to the size and shape of the tablet to be formed. Surprisingly however, applicant found that a cavity may be used that has a volume smaller than that of the tablet to be formed. In this embodiment the pellet projects from the surface of the element, out of the cavity. This is enabled i.a. since the fluid formulation is rapidly cooled by the conductive contact with the cold element. This helps to ensure that a pellet can be formed that even sticks out of the cavity. An advantage of this particular embodiment is that the pellet can be removed relatively easy from the cavity since the contact surface between the pellet and cavity is small when compared to a pellet that is completely enclosed by or sunk in the cavity. Another advantage of this embodiment is that there may be provided a discontinuity in the physical appearance of the tablet corresponding to the transition site between the cavity and the open space above the cavity. Since the pellet to be formed sticks out of the cavity, there may be provided a discontinuity in the shape of the pellet at the cavity entry. Such a discontinuity may be used to distinguish the tablet from other tablets (thus being for example an alternative for a company logo, icon or colour), or may be used to provide advantageous mechanical properties.

In a preferred embodiment, the volume of the cavity is smaller than 50% of the volume of the pellet. In this embodiment, more than half of the pellet sticks out of the element in which the cavity is formed. This makes removal of the pellet very easy. A minimum volume to ensure a practically adequate heat extraction from the fluid formulation is about 15%, preferably about 20%.

In an embodiment, a measure is taken to support automatic detachment of the pellet from the cavity wall. Automatic detachment, i.e. without mechanical intervention of any kind, significantly reduces the chances that a pellet will be damaged upon removal from its corresponding cavity. In an embodiment wherein the cavity is formed in a solid element, the automatic detachment is supported by keeping the temperature of the solid element adequately beneath the freezing temperature of the fluid formulation. It has been found that for every fluid formulation, a temperature can be found which is that low, that it generates a speed of shrinkage of the pellet sufficient to induce automatic detachment of the pellet from the cavity wall. For a water based fluid formulation, the temperature should be at least 80 degrees (K) below the freezing point of the formulation, thus about −80° C. Preferably the difference is about 100-120 degrees up to even 196 degrees. The difference needed depends on the constitution of the formulation but can simply be found by increasing it from 0, until automatic detachment is provided. Such detachment can be recognised easily since upon automatic detachment, the pellet can be simply removed from the cavity using merely gravitational forces (turning the element upside down). In another embodiment the automatic detachment is supported by providing the cavity wall with an abhesive surface by chemical and/or physical means. Commonly known chemical means for obtaining an abhesive surface are for example coatings with a high fluorine content (Teflon® for example) or high silicone content. Physical means are for example lotus leaf-like structures or commonly known nanopins. An abhesive surface has the additional advantage that the pellet can be formed in a very shallow cavity. However, a disadvantage is that complete wetting of the surface to form a negative print of the cavity wall is inherently difficult to achieve.

In an embodiment the pellet is taken out of the cavity by applying a pushing force to the pellet. It has been found that applying a pushing force, despite inherent risk of mechanically damaging the frozen pellet, provides excellent results with regard to removing a pellet from the cavity while keeping its shape intact. The advantage of a pushing force over for example a stream of blowing gas is that pushing can be done with a clean mechanical element, while a stream of air has inherent sterility problems. In a preferred embodiment the pellet is pushed out of the cavity using a tangentially directed force. It was found that a tangential force, although less direct, has the advantage that there is less mechanical impact on the pellet, while even improving the removal process. By applying a tangential force, the pellet can start to twist and turn in its cavity which will lead to easy and reliable removal without damaging the pellet.

In an embodiment multiple pellets are placed in a packed bed before the pellets are dried in the vacuum. In this embodiment the pellets are not dried while arranged in a single layer, but are packed to be part of a multiple layer bed. This way the drying step, which may take place in a lyophiliser, is operated at a significantly higher efficiency. However, since the drying process depends inter alia on heat transfer through the bed, the number of layers will be restricted to 2 or 3. In a further embodiment therefore, the pellets are packed in a heat conducting container having a bottom and side walls, and a heat source is provided above a top layer of the packed pellets, the heat source having a surface directed to a top layer of the bed, which surface has an emissivity coefficient of at least 0.4, whereafter the pellets are subjected to the vacuum while at the same time heating at least the bottom of the container and the said surface to provide heat to the particles to support drying of the pellets. In this embodiment the number of layers in the bed can be increased to be over 3. The emissivity coefficient (usually denoted as E) in this respect is the ratio of energy radiated by the surface to energy radiated by a true black body of the same temperature. It is a measure of the ability to absorb and radiate energy. A true black body would have an $\epsilon=1$ while any real surface or object would have an $\epsilon<1$. Emissivity is a numerical value and does not have units. By having an emissivity coefficient of at least 0.4, the heated surface radiates relatively high quantities of heat to the particles. Emissivity in the sense of the present invention is the mean emissivity as established at four different temperatures of the surface, viz. 55, 60, 65 and 70° C. The emissivity can be measured by using dedicated emissivity measurement equipment as commercially available such as the Model 205WB of Advanced Fuel Research Inc., East Hartford, Conn. USA. Such equipment however is very expensive. Alternatively, as commonly known, a very simple way of measuring the emissivity is to heat the surface and a surface with a known emissivity to the same temperature as determined by a thermocouple. Then read the temperature of the two surfaces with a standard infrared pyrometer. The difference in the two infrared temperature measurements is due to the difference in the emissivities of the surfaces (see also Applied Optics, Vol. 13, No 9, September 1974).

As mentioned here-above, an embodiment of the method according to the present invention is specifically advantageous for obtaining so called orally disintegrating tablets (viz. the embodiment wherein the formulation is cooled by extracting heat from the formulation through a cavity wall by conduction). In an embodiment of this specific process to obtain ODT's, the formulation comprises a crystalline carrier material that is solid at room temperature and a gelator. A crystalline carrier has the advantage that it can be easy formulated into a fluid formulation, and that it provides good mechanical properties to the tablet. The gelator is incorporated to even further improve the mechanical properties of the tablet. Examples of suitable carrier materials are sugars such as mannitol, dextrose, lactose, galactose, trehalose and cyclic sugars such as cyclodextrin, inorganic salts such as sodium phosphate, sodium chloride and aluminium silicates, amino acids typically having from 2 to 12 carbon atoms such as glycine, L-alanine, L-aspartic acid, L-glutamic acid, L-hydroxyproline, L-isoleucine, L-leucine and L-phenylalanine. The gelator may be any agent that is capable of forming a network of molecules within a fluid to provide the fluid the consistency of a gel. Such an agent may comprise high molecular proteins or other polymers but may also be based on small molecules that can form networks through recombination of the small molecules into long chains (as known i.a. from U.S. Pat. No. 6,471,758). The gelator has the advantage that the large molecules provide additional mechanical stability to the final tablet. Typical examples of gelators are gelatins, dextrins and soy-, wheat- and psyllium seed proteins, gums such as guar, agar, acacia, xanthan and carreagenan, polysachharides, alginates, carboxymethylcelluloses, pectins, polyvinylpyrrolidone etc.

In a further embodiment the formulation comprises 3 or more weight percent of the crystalline material and about 4 weight percent of the gelator. Typically the amount of a crystalline carrier material in a formulation to obtain an ODT is kept below 3 weight percent. For the gelator an amount of about 4 weight percent is used. Applicant found that when using 3 or more weight percent of the crystalline carrier and at the same time using about 4 weight percent of the gelator, surprisingly leads to a high mechanical strength of the final tablet in combination with very good disintegration properties.

In an embodiment the gelator comprises a non gel-forming material, preferably a collagen derived material, such as a gelatine. A non gel-forming material is a material that at a concentration of 4% (w/w) in a fluid formulation (in particular water), at a temperature at which that fluid formulation is used for dosing purposes (in the present case for filling cavities at room temperature, 20° C.), does not form a gel in the said fluid formulation when left in a stationary situation for 24 hours. Although the gelator in principle is capable of forming a gel in a liquid, we found that it is advantageous to choose a gelator that not, or at least not completely, forms a gel in the liquid formulation when filling the cavity (this can be simply accomplished by choosing a gelator that dissolves in the fluid formulation at the said temperature in stead of forming a network of gelator molecules in the fluid). This simplifies the dosing of the fluid formulation, given the less high viscosity and/or the less non-Newtonian behaviour of the fluid formulation. After dosing, upon lowering the temperature the gelator will form a gel. In a preferred embodiment the collagen derived material is a gelatin having a weight average molecular weight of $2 \times 10^4$ g/mol (thus having an actual average weight between 15.000 and 25.000 g/mol). Applicant found that the use of such a gelator may lead to less sticky tablets, and also, to tablets having very good disintegration properties while keeping adequate mechanical strength despite the relatively low molecular weight of the gelator. Gelati Sol P (Gelita, Eberbach, Germany) is a good example of such a gelator.

SPECIFIC EXAMPLES OF THE INVENTION

Figure 1B:
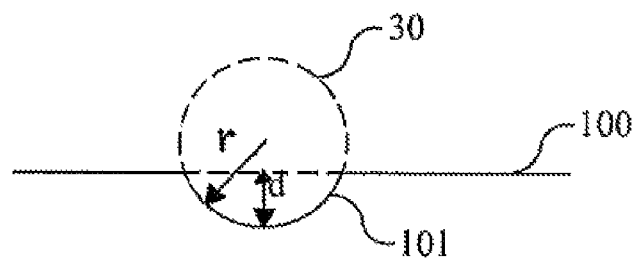
Figure 1C:
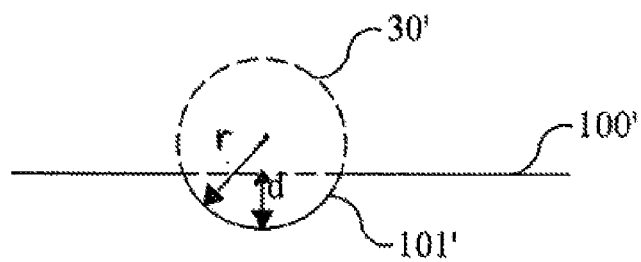
Figure 2:
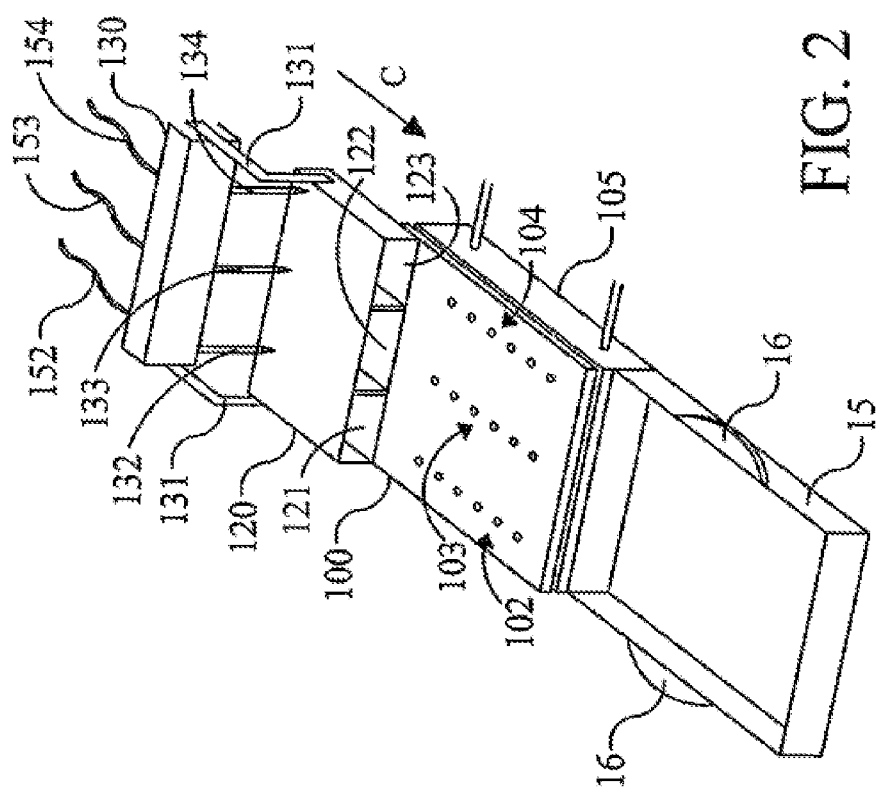
Figure 3:
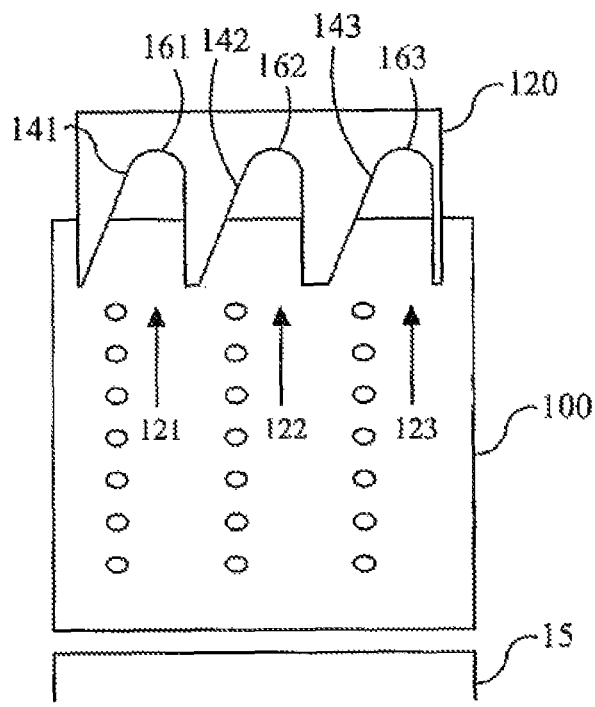

The invention will now be explained in more detail used the following non-limiting examples FIG. 1 schematically shows a cavity tray and corresponding cooling element for use in a method to obtain frozen pellets FIG. 2 schematically shows the basic parts of an apparatus for obtaining frozen pellets FIG. 3 is a schematic top plan view of parts of the apparatus as depicted in FIG. 2

Figure 4:
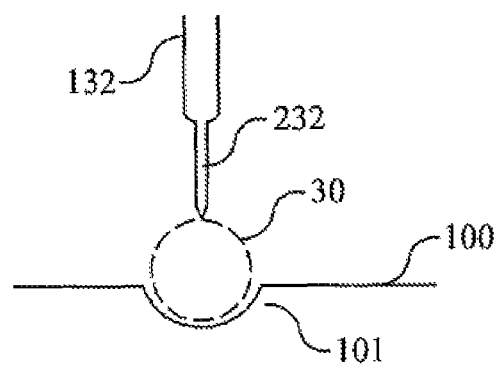
Figure 5:
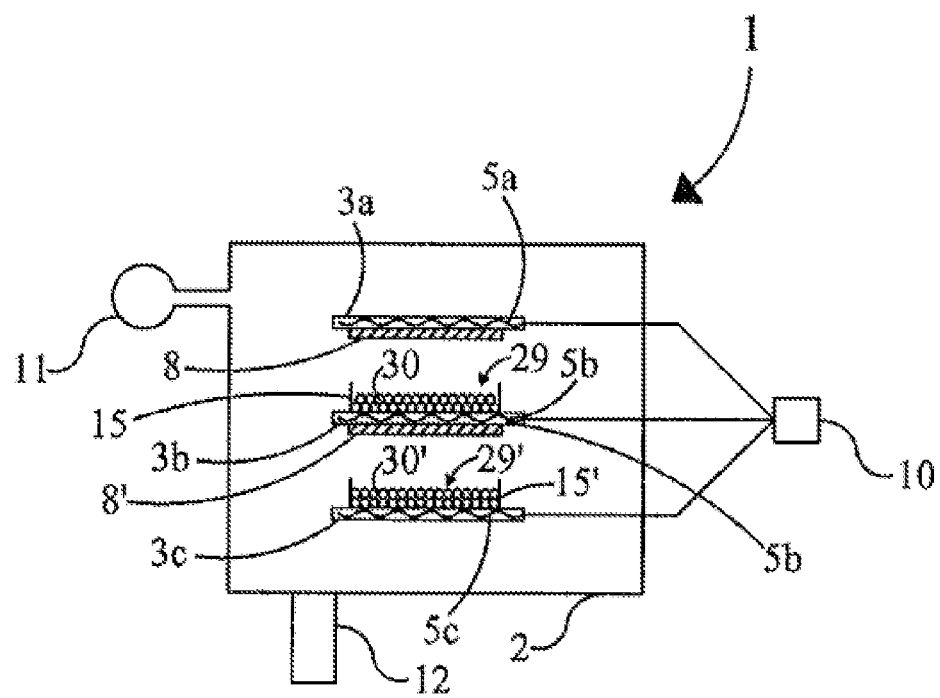
Figure 6:
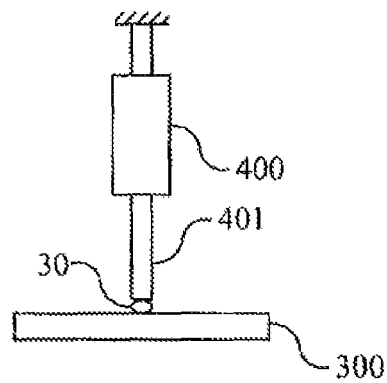
Figure 7:
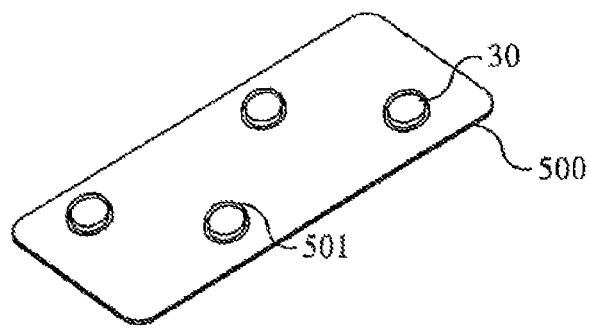
Figure 8:
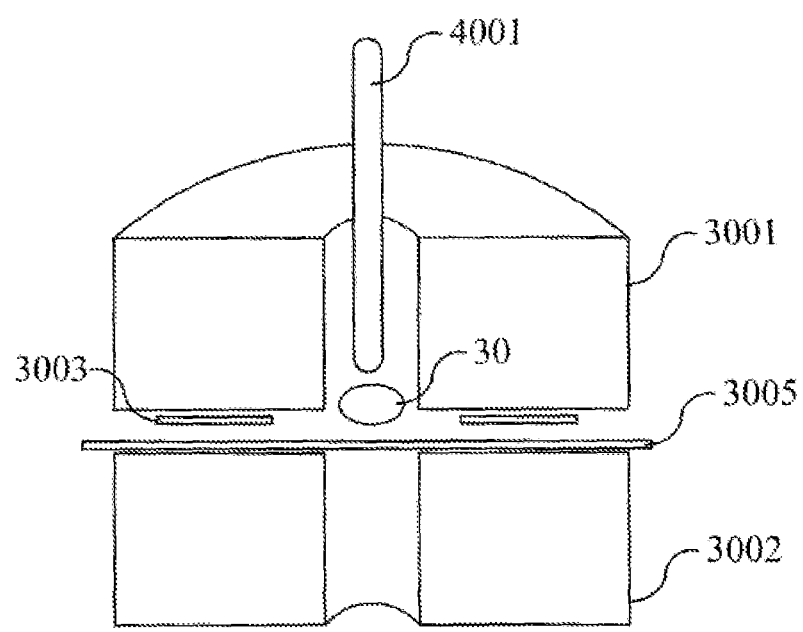

FIG. 4 schematically depicts a filling needle in conjunction with the corresponding cavity FIG. 5 schematically shows a drying chamber for use in the present method and system FIG. 6 schematically shows a tensile tester for establishing the crushing strength of a tablet FIG. 7 schematically shows a package containing a tablet according to the invention FIG. 8 schematically shows a device to measure the stability of tablets when being pressed through a foil.

FIG. 9 schematically shows examples of tablets being pressed through a foil.

Example 1 Obtaining tablets with a vaccine component
Example 2 Obtaining tablets containing a chemical drug
Example 3 Establishing the mechanical stability of a tablet
Example 4 Alternative way of establishing the mechanical stability of an ODT

FIG. 1

FIG. 1A schematically shows a cavity tray 100 and corresponding cooling element 105 for use in a method to obtain frozen pellets. Cavity tray 100 is a solid steel plate (made of stainless steel, grade 316L) having a thickness of 6 mm. In the plate three rows (102, 103 and 104) of cavities 101 are formed. FIG. 1B gives an example of a first type of cavity. The shown cavity 101 has a spherical shape, a radius r of 2.9 mm and a depth d of 2.1 mm. In such a cavity, a spherical pellet 30 with a volume of about 100 µl (having a radius of about 2.9 mm) can be formed. Another example, which can be used for larger tablets, is shown in FIG. 1B. This cavity 101' is also spherical, has a radius r of 4.9 mm and a depth of 4.0 mm. In such a cavity a spherical pellet 30' with a volume of about 500 µl (having a radius of about 4.9 mm) can be formed. Indeed, other sizes (for example between 50 µl and 1000 µl) and shapes can also be provided for, for example to obtain an oblate (also known as "M&M-" or "Smartie-" shaped) pellet, an egg-shaped pellet, an oval (zeppelin-shaped) pellet etc. In particular, an oblate pellet can be formed in an oblate cavity having a length and width of 6.0 mm and a depth of 3.3 mm by dosing a volume of about 300 µl.

Tray 100 rests under gravitational forces on cooling element 105 (in an alternative embodiment, the tray can be clamped to cooling element 105). This element is a hollow stainless steel box, having a height of about 6 cm. The box 105 has an entrance 106 and an outlet 107. Through the entrance 106, liquid nitrogen can be supplied (indicated by the arrow A) at a temperature of about −196° C. At the outlet 107 nitrogen (a mixture of liquid and gas) leaves the box 105 (indicated by the arrow B). This way the tray 100 can be cooled adequately to obtain a very fast solidification process when a fluid formulation is dispensed in one (or more) of the cavities 101. Depending i.a. on the temperature of the fluid formulation, the temperature of the surrounding air, the nitrogen flow and the speed at which solid pellets are produced, an equilibrium temperature of between −85° C. and −145° C. for the tray 100 can be obtained in the shown arrangement.

FIG. 2

FIG. 2 schematically shows the basic parts of an apparatus for obtaining frozen pellets. The same tray 100 and cooling element 105 as depicted in FIG. 1 can be seen. At the front (downstream of the tray 100) a black plastic container 15 is shown, which container has handles 16 for manually handling the container. This container 15 is placed directly against cooling element 105. The container is cooled to a temperature of about −45° C. by having its support (not shown) cooled by using liquid nitrogen. At the other side of the tray 100 (upstream side) a collecting element 120 is shown, which element is divided into three compartments 121, 122 and 123. This element travels over the surface of tray 100 (with a space of about 0.2 mm between the bottom of element 120 and the surface of tray 100) in the direction C and pushes frozen pellets out of their cavities. These pellets are then collected in each of the compartments 121, 122 and 123 and are ultimately brought over into container 15. Attached to collecting element 120, via brackets 131, is dispensing unit 130. This unit comprises three needles 132, 133 and 134, corresponding to cavity rows 102, 103 and 104 respectively. The needles are used to dispense the fluid formulation in each of the cavities. The fluid formulation is supplied to each of the needles via tubes 152, 153 and 154 respectively.

When operating the device, the atmosphere is cooled to a temperature of around 15° C. using dry nitrogen gas. Because of this relatively high temperature of the surrounding atmosphere, a water based fluid formulation can be handled in and around the apparatus without the risk that the formulation freezes in the tubes 152, 153, 154 or the needles 132, 133 an 134. Dry nitrogen gas is used to prevent crystallization of water into ice on the various parts that are kept below 0° C. In this setup, the tray 100 will have an equilibrium temperature of about −125° C. The collecting element 120 has a temperature around −35° C., and the container 15 will have a temperature of about −45° C.

The process starts with moving the element 120 in the direction C until the needles coincide with the first (upstream) cavities. Then the movement of element 120 is temporarily stopped, and the first three cavities are filled with fluid formulation. When finished, the element 120 moves forward until the needles coincide with the next three cavities. Then, these cavities are filled with fluid formulation. This process continues till all cavities are filled with the fluid formulation. Then the element 120 is lifted somewhat (about 25 mm) and brought back to its original position at the upstream part of the tray 100. Then the element 120 travels forward again in the shown direction C. This time, the element will come across frozen pellets in each of the cavities. The pellets are pushed out of their cavities and collecting in the compartments 121, 122 and 123 respectively. In this process, each pellet may remain between 20 and 90 seconds in its cavity (from filling until pushing out, depending i.a. on the size of the pellet: the larger the pellet, the longer the solidification process will take). At the same time, upstream of element 120, the emptied cavities are refilled as described here-above. This process continues until container 15 is adequately filled with frozen pellets.

FIG. 3

FIG. 3 is a schematic top plan view of parts of the apparatus as depicted in FIG. 2. In this schematic view, the inner arrangement of collecting element 120 is shown. Each compartment 121, 122 and 123 comprises an inner slanted wall 141, 142 and 143 respectively. Each of these walls is slanted with respect to moving direction C with an angle of 10°. The walls hit the frozen pellets and push them out of their cavities. Since each wall is slanted, the pellets are pushed out with a tangentially directed force. This has the advantage that the pellets are more or less twisted out of their cavities. It has appeared that this significantly reduces the risk of pellets being damaged. When they are pushed out, the pellets are collected at the back of the compartments, in this case in roundings 161, 162 and 163 respectively. At the downstream position of the element 120 (adjacent container 15) the pellets will automatically fall into container 15.

FIG. 4

FIG. 4 schematically depicts a filling needle in conjunction with the corresponding cavity. The needle 132 has a tip 232. This tip 232 is arranged to have a vertical position with respect to the surface of tray 100, such that the tip coincides with the uppermost part of the pellet 30 to be formed in cavity 101. From this position, the cavity is filled with fluid formulation. The speed of filling can be tuned to obtain any desired filling process. For example, when a very low speed is chosen, a rather irregular shaped pellet will be formed, i.a. since the fluid will not be able to completely wet the cavity wall. When a sufficiently high speed is chosen a complete wetting can be achieved. This speed depends i.a. on the actual temperature of the fluid at the time of filling the cavity, the cavity wall temperature, the viscosity of the fluid etc. For each formulation this speed can be found by performing routine experiments. After the required amount of fluid formulation is filled, the needle travels further to the next cavity. However, it is preferred that a waiting time, for example about 0.1 seconds, is used between the moment when all formulation has been dispensed and the moment at which the needle starts traveling again. This may prevent mechanically disturbing the dosed pellet. It is noted that in this particular example a spherical pellet 30 is depicted. However, other shapes can also be formed. In any case, the optimal position for the tip is right at the uppermost part of the pellet to be formed.

FIG. 5

In FIG. 5 a lyophiliser (freeze-dry apparatus) is schematically depicted. Such a lyophiliser could for example be the Christ Epsilon 2-12D as available from Salmen Kipp, Breukelen, The Netherlands. The lyophiliser 1 comprises a housing 2 and multiple shelves 3. The Epsilon 2-12D comprises 4+1 shelves, for matters of convenience three of these shelves (viz. shelves 3a, 3b and 3c) are shown in FIG. 1. Each of these shelves is provided with a heating element 5 (referred to with numerals 5a, 5b and 5c respectively) for even heating of the shelves 3. The heating is controlled by making use of processing unit 10. The housing is connected to a pump unit 11 for providing adequate low pressure within the housing 2. The interior of the housing can be cooled to a temperature as low as −60° C. by using cooling unit 12, in particular containing a condenser (in fact, it is the condenser that is kept at about −60° C., which acts as a driving force for condensation of sublimated ice). Shelves 3a and 3b are provided with black PTFE plates 8 and 8' fixed to their bottom. The emissivity coefficient of these plates is 0.78. By intimate contact between these black plates and the shelves, these plates can be warmed virtually to the same temperature as the shelves themselves. This way, the plates 8 can be regarded as heat source in addition to the shelves 3 themselves.

Placed on the shelves are container 15 and 15'. These containers are made of a heat conducting material, in this case carbon black filled polyethyleneterephtalate. The containers are in a heat conducting contact with the shelves on which they rest. In the shown arrangement, the containers are filled with frozen pellets 30 which thus form a bed 29 of packed pellets in each container. By heating the shelves, the particles may receive heat via the heated bottom and side walls of the containers and by irradiation from the heated plates 8 and 8' respectively. It is noted that each container 15 has a width and length of about 20 to 30 cm and a height of about 4 cm. The height of the packed bed after filling the container is typically 1.5 to 3 cm. This leads to typical values for an aspect ratio of the bed of between 20/3≈7 to about 30/1.5=20. However, monolayer arrangement of pellets can also be used.

FIG. 6

FIG. 6 schematically shows a tensile tester for establishing the crushing strength of a tablet. This figure is a schematically side view of a LR5K Plus tensile tester (available from Lloyd Instruments, UK), with a load cell 400, to test the crushing strength of a tablet 30. For this, the tablet 30 is being subjected to a load force with rod 401 while it rests on support 300.

FIG. 7

In FIG. 7 a package 500 containing a tablet according to the invention is schematically shown. Package 500 comprises a rectangular base and multiple blisters 501 having contained therein tablets 30. The blister package can be of the peel-off type, wherein a layer (not shown) fixed to the rectangular base can be peeled off to open each one of the blister to take the respective tablet out. Also, in particular when the mechanical stability of the tablet is sufficient, the layer can be of a more conventional type (often aluminum foil) wherein each tablet is pushed through the layer.

FIG. 8

FIG. 8 schematically shows an alternative device to establish the mechanical stability of an ODT. With this device the propensity of freeze dried tablets to remain intact after being pressed through a foil. Dies 3001 and 3002 are units that contain cylindrical holes of 13 diameter. An aluminium foil 3005 with a thickness of 5 μm is placed between the dies and covered by a rubber ring 3003 to prevent movement of foil. A freeze dried tablet 30 is placed on the foil and can be pressed through the foil using a glass rod 4001 by exerting a manual force on the rod. After pressing tablets through the foil, either complete tablets or fragments of tablets can be collected below die 3002.

FIG. 9

Figure 9A:
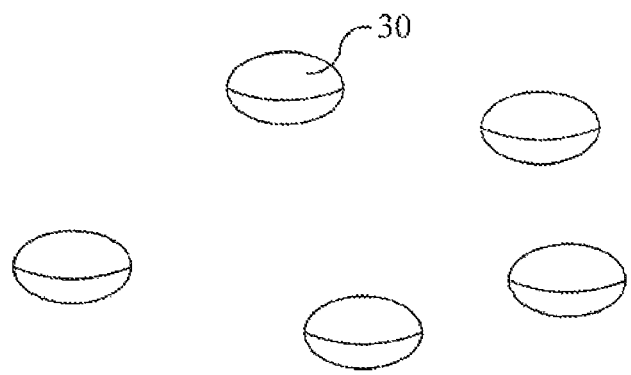
Figure 9B:
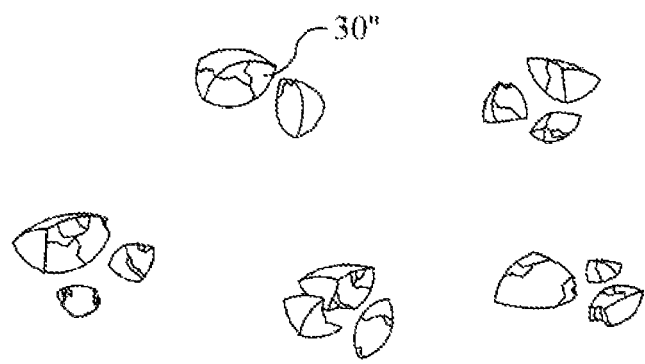

FIG. 9 shows examples of tablets or fragments of tablets after performing the test to measure the propensity to remain in tact after being pressed through a foil. FIG. 9a shows tablets 30 that remain intact when being pressed through a 5 μm foil. FIG. 9b shows tablets 30" that are fragmented when being subjected to the same test.

Example 1

To obtain tablets for vaccine formulation, live virus was harvested from eggs. The allantois fluid containing the virus (either IB or ND; see table 2) was mixed with a stabilizer. The stabilizer is known from WO2006/094974 A2, and in particular described in Table 5 of that patent application (with a glycine content of 160 g/l). The method of adding the stabilizer is also described in that patent application, namely in the general outline of the introductory part of the "Examples" section on page 24.

A plate is used having three rows of cavities according to FIG. 1B. In each of these cavities about 100 μl of fluid formulation is dispensed in approximately 0.3 seconds. The formulation will start the freeze immediately upon contacting the cavity wall. However, it takes approximately 15 seconds before the pellet is substantially frozen such that it can be mechanically handled. After this, the pellets (which have a diameter of approximately 5.7 mm) are pushed out of the cavities (as explained in conjunction with FIGS. 2 and 3) and transferred to freeze-dry container 15.

The frozen pellets (having a temperature of about minus 45° C.) are arranged in the container 15 in the form of a packed bed with an aspect ratio of about 15. Multiple containers are then put in the lyophiliser (see FIG. 5) which has beforehand been brought to a temperature of about −35° C. The lyophiliser is subjected to the following freeze-drye cycle (Table 1).

TABLE 1

| Phase | Time [h:m] | Temp [° C.] | Vacuum [mbar] |
|---|---|---|---|
| Freezing | 00:30 | −35 | 1000 |
| Preparation | 00:20 | −35 | 1000 |
| Initial sublimation | 00:10 | −35 | 0.370 |
| Sublimation 1 | 03:00 | 40 | 0.370 |
| Sublimation 2 | 16:00 | 40 | 0.370 |
| Closing step | 00:01 | 4 | 0.021 |

As can be seen in Table 1, after loading the shelves with the filled containers the shelves are firstly kept at a temperature of −35° C. for 30 minutes (the "Freezing" phase). Herewith the frozen pellets are brought to a temperature of −35° C. The pressure is kept atmospheric. Then, the temperature of the shelves is stabilized at −35° C. during 20 minutes, pressure is still atmospheric ("Preparation"). Then, the pressure is lowered to 0.370 mbar in a period of ten minutes, the temperature of the shelves is kept at −35° C. ("Initial sublimation"). Under these conditions, the frozen liquid already sublimates and heat is supplied to the pellets by the two heat sources via conduction and irradiation respectively. However, the speed of sublimation under these conditions is relatively low. To increase the speed of sublimation, the shelves are brought to a temperature of 40° C. in a period of 3 hours ("Sublimation 1"), and kept at that temperature for 16 hours ("Sublimation 2"). The pressure is kept at the low value of 0.370 mbar. Thereafter, the pressure is further reduced to 0.021 mbar whilst the temperature of the shelves is brought to 4° C. This latter step takes 1 minute ("Closing step"). After that, the sublimation process is completed and about 98% of the frozen liquid has left the pellets, thereby transforming into fast-disintegrating tablets. Then, dried nitrogen gas with a temperature of about 20° C. is led into the lyophiliser until the pressure is about atmospheric. This takes about 2 minutes. Then the door can be opened to take out the tablets. When using the present method, it can be seen that a homogenous lyophilising result can be obtained, visible as a homogenous bed of lyophilized pellets. After opening the lyophiliser, the tablets are preferably not subjected to a humid environment to try and prevent condensation of water on the tablets. In particular, the tablets are filled in containers in a closet with an atmosphere of dried air or nitrogen. After filling the containers, they are closed and stored in a cool place (4-8° C.) until further use.

This way, lyophilized spherical tablets can be obtained with an average diameter of approximately 5⅜ mm and having contained therein a vaccine ingredient as shown in Table 2.

TABLE 2

| Pharmaceutical component | Dose of active component per particle [$\log^{10} \text{EID}_{50}$] |
|---|---|
| Live Infectious Bronchitis virus, strain 4-91 | 6.6 |
| Live infectious bronchitis virus, serotype Massachusetts, Ma5 | 6.5 |
| Live infectious bronchitis virus, serotype Massachusetts, H120 | 6.0 |
| Live Newcastle Disease virus | 8.5 |
| Live Newcastle Disease virus | 9.0 |

The tablets can be used to provide a pharmaceutical pack. This pack consists of a container (such as a glass or plastic vial) containing one or more of the tablets and optionally other constituents. The vaccine ingredient in the tablets can be administered to an animal as follows.

For the IB tablets, firstly one or more of these tablets are reconstituted in a volume of physiological saline solution, upon which the tablets immediately disintegrate (within 60 seconds). The resulting vaccine can be administered to chickens by means of a standardized dropper into a nostril or eye. For the ND tablets, these can be mixed with a volume of cool clean water. The resulting vaccine can be administered to chickens via a spray method or via the drinking water.

Example 2

To obtain tablets containing a chemical drug a plate can be used having three rows of cavities according to FIG. 1C. In each of these cavities about 500 μl of fluid formulation is dispensed in approximately 2 seconds. At this dosing speed the cavity wall is completely wetted and thus the surface of the part of the pellet that is in the cavity (before the pellet is taken out of the cavity) is a negative print of the surface of the cavity, in this case a smooth surface without indentations or wrinkles. If a logo (either positive or negative) would have been present in the cavity, that logo would have been visible on the surface of the pellet. Examples of fluid formulations which can be used to make frozen pellets are given herebeneath:

Fluid formulation 1: 2 weight percent asenapine ((3aS,12bS)-5-Chloro-2,3,3a,12b-tetrahydro-2-methyl-1H-dibenz[2,3:6,7]oxepino[4,5-c]pyrrole maleate (1:1); ORG 5222), 4 weight percent hydrolyzed gelatin (available from Croda, Yorkshire, England), 3 weight percent mannitol (PEARLITOL®, type C160, available from Roquette, Lestrem, France), and water QS (quantum sufficiat, i.e. added to complete 100% total weight).

Fluid formulation 2: 16 weight percent SCH 530348 bisulfate thrombin receptor antagonist (TRA; see U.S. Pat. No. 7,235,567), 3.5 weight percent hydrolyzed gelatin, 3 weight percent mannitol, 3.73 weight percent sodium citrate dihydrate, 1.41 weight percent citric acid monohydrate, and water QS.

Fluid formulation 3: 8 weight percent TRA, 8 weight percent gelatin (Sol P, available from Gelita, Eberbach, Germany), 9 weight percent mannitol, 3.73 weight percent sodium citrate dihydrate, 1.41 weight percent citric acid monohydrate, and water QS.

Fluid formulation 4: 8 weight percent TRA, 8 weight percent gelatin (Sol P, available from Gelita, Eberbach, Germany), 9 weight percent mannitol and water QS.

The formulation will start to freeze immediately upon contacting the cavity wall. However, it takes approximately 45 seconds before the pellet is substantially frozen such that it can be mechanically handled. After this, the pellets (which have a diameter of approximately 9.8 mm) are pushed out of the cavities (as explained in conjunction with FIGS. 2 and 3) and brought over in freeze-dry container 15.

The frozen pellets (having a temperature of about minus 45° C.) are arranged in the container 15 in the form of a densely packed monolayer. Multiple containers are then put in the lyophiliser (see FIG. 5) which has beforehand been brought to a temperature of about −35° C. The lyophiliser is subjected to the following freeze-drye cycle (Table 3).

TABLE 3

| Phase | Time [h:m] | Temp [° C.] | Vacuum [mbar] |
|---|---|---|---|
| Freezing | 00:30 | −35 | 1000 |
| Preparation | 00:30 | −35 | 1000 |
| Initial sublimation, part 1 | 00:10 | −35 | 0.310 |
| Initial sublimation, part 2 | 05:00 | −15 | 0.310 |
| Sublimation 1 | 07:00 | 10 | 0.310 |
| Sublimation 2 | 24:00 | 35 | 0.310 |
| Closing step | 00:01 | 35 | 0.310 |

As described here-above, after the "Closing step", the sublimation process is completed and about 98% of the frozen liquid has left the pellets, thereby transforming into fast-disintegrating tablets. Then, dried nitrogen gas with a temperature of about 20° C. is led into the lyophiliser until the pressure is about atmospheric. This takes about 2 minutes. Then the door can be opened to take out the tablets. The tablets are filled in containers in a closet with an atmosphere of dried air or nitrogen. After filling the containers, they are closed and stored in a cool place (4-8° C.) until further use.

The disintegration of the resulting tablets can be tested by putting a tablet in a beaker filled with water having a temperature of 37° C., and measuring how long it takes before the tablet is in essence fully disintegrated (no large pieces visible with the naked human eye). It appears that all tablets made with the fluid formulations 1, 2, 3 and 4 disintegrate within 5-10 seconds.

Example 3

In this example various methods to assess the mechanical stability of a tablet are described. The first test is a tablet friability test which is commonly used for testing the vulnerability of tablets towards mechanical handling. An apparatus and method to unambiguously asses this friability is available from DeltaLab, Moirans of France: the A4113 Tablet Friability and Abrasion Tester. Other apparatus and methods are commercially available as well.

A method for assessing another property that may be used to characterize the mechanical stability of a tablet is establishing the crushing strength of a tablet. The principle of this testing method is that a strain is put on a tablet and the resulting force is measured until the tablet is completely crushed. For this a LR5K Plus tensile tester of Llyod Instruments (Fareham, Hants, UK) can be used. In the present example we used the XLC 50N load cell (see FIG. 6). The punch displacement (also called "extension") speed was 10 mm/min. Force-displacement profiles were detected in three-fold and breakage patterns were determined with Nexygen software which has been supplied with the tester. It is noted that as an alternative, the crushing strength could be measured with the Pharmatest PTB 300/301 (available from Pharmatest, Hainburg, Germany).

In a first experiment a series of 250 µl spherical placebo tablets (containing no medicinal substance) has been made with a method as described here-above (Example 2), differing however in the size of the cavities: the radius is 3.9 mm and the depth is 3.0 mm. Various fluid formulations were used, each comprising a different amount of the gelator Gelita Sol P (Gelita, Eberbach, Germany) and crystalline carrier mannitol (PEARLITOL®, type C160, obtained from Roquette, Lestrem, France) to arrive at various different tablets. Apart from these compounds the fluid formulations comprised water. In table 5 the various compositions are shown.

TABLE 5

| Batch | gelatin (w %) | mannitol (w %) | water QS |
|---|---|---|---|
| Sol P1 | 4 | 3 | 93 |
| Sol P2 | 4 | 6 | 90 |
| Sol P3 | 4 | 9 | 87 |
| Sol P4 | 8 | 3 | 89 |
| Sol P5 | 8 | 6 | 86 |
| Sol P6 | 8 | 9 | 83 |
| Sol P7 | 12 | 3 | 85 |
| Sol P8 | 12 | 6 | 82 |
| Sol P9 | 12 | 9 | 79 |

When a tablet is being assessed for its crushing strength with the Llyod Instruments LR5K tensile tester, firstly the load is increased with the extension. After some time, when the tablet fails (i.e. breaks), the increase of the load stops or even decreases. The maximum load at the time of failure is called the crushing strength. The results of the measurements of the crushing strengths of the tablets are depicted in Table 6.

TABLE 6

| Formulation | Average crushing strength (N) |
|---|---|
| Sol P1 | 0.71 |
| Sol P2 | 1.81 |
| Sol P3 | 2.39 |
| Sol P4 | 4.11 |
| Sol P5 | 2.68 |
| Sol P6 | 4.39 |
| Sol P7 | 5.89 |
| Sol P8 | 4.45 |
| Sol P9 | 4.19 |

What can be seen is that the average crushing strength is relatively high for these tablets (which are all based on fluid formulation comprising 3 or more weight percent of a crystalline carrier and 4 or more weight percent of a gelator).

In a second experiment a series of 500 µl oblate tablets, optionally containing TRA (as mentioned under Example 2) as medicinal substance, has been made with a method as described here-above (Example 2), differing however in the size of the cavities: the radius is 12.0 mm and the depth is 3.0 mm. Various fluid formulations were used, each comprising a different amount of the gelator Gelita Sol P (Gelita, Eberbach, Germany) and crystalline carrier, composed of various amounts of mannitol (PEARLITOL®, type C160, obtained from Roquette, Lestrem, France) and sucrose (α-D-glucopyranosyl-β-D-fructofuranoside). Apart from these compounds the fluid formulations comprised water QS. In table 7 the various compositions are shown.

TABLE 7

| Batch | gelatin (w %) | mannitol (w %) | sucrose (w %) | TRA (w %) |
|---|---|---|---|---|
| K | 8 | 9 | 2 | — |
| L | 8 | 9 | 4 | — |
| M | 8 | 12 | 2 | — |
| N | 8 | 12 | 4 | — |
| O | 8 | 9 | 2 | 8 |
| P | 8 | 12 | 2 | 8 |

It appeared that the crushing strength of each of the tablets was the same, about 5N. This means that the additional sucrose nor the medicinal substance have a significant influence on the strength of the tablets in this experiment. The amount of 8 weight percent gelatin and over 9 weight percent mannitol (9 or 12%) therefore, which was found to give a very good crushing strength in the first experiment, appears to be very suitable for a tablet, in particular for a tablet that needs to have a high mechanical stability per se.

Example 4

The propensity of tablets to remain intact after being pressed through a foil has been determined using the device as described in conjunction with FIG. 8. This test is referred to as the "push through test" in this example. Tablets of different compositions were produced. Amounts and ratios of two types of gelatin were varied to obtain a gelator, in line with data published by Chandrasekhar, R., Hassan, Z., AlHusban, F, Smith, A. M and Mohammed, A. R. Eur. J. Pharm. Biopharm 72 (2009) 119-129. Two types of gelatin were used: Sol P (a non gel-forming gelatin) and BS100 (a gel-forming gelatin, i.e. a gelatin that at a concentration of 4% (w/w) at the dosing temperature of the fluid formulation, forms a gel in the said fluid formulation when left in a stationary situation for 24 hours). The latter gelatin is available from Gelita, Eberbach Germany. The amount of mannitol (PEARLITOL®, type C160), was kept at two levels. All tablets contained 2% (m/v) of a drug, in this case asenapine (see Example 2). Oblate, spherical and flat tablets with a volume of 250 μl were made and tested in the push through test.

For comparison, a commercially available 250 μl tablet ("Tablet") was also tested. This tablet contained 2% of a drug, 4% of an unknown gelator and 3% mannitol. After testing, tablets were either intact or fractured into numerous pieces, which is illustrated by the schematic drawings in FIG. 9. Table 8 summarises the results and presents the percentage of tablets intact when 10 pellets of each composition and specific shape and volume were tested. It is noted that ODT's are in general so friable that it is commonly understood that no tablets will remain intact in the chosen set-up. Surprisingly however, it was found that using the present invention, tablets can be made that remain intact when being pressed through a 5 μm thick aluminium foil.

The results in table 8 also imply an effect of the shape of the tablet to survive the push through test. The oblate and spherical shapes in general seem to be superior compared to flat tablets. It is possible to express surface curvature relative to the diameter of the unit. The dosing principle of the method according to the invention, together with the fact that the liquid dosed has a certain surface tension implies that the surfaces of the tablets can be described as two hemispheres in the case of spherical tablets and two connected spherical caps in the case of oblate tablets. For reason of the fact that the pellets shrink during freeze drying or during storage, or both, the dosing volume is not an adequate prediction of the future dimensions of the tablets. It is possible to calculate the radius of curvature of the cap and correlate that to the diameter of the tablet using the dimensions of the tablet, using widely available information that correlates dimensions of a cap with its volume. For example, the relative curvature K of the tablet is defined by the ratio of the radius of curvature (R) of the cap and half the diameter of the tablet (D):

$$K=2R/D$$

Higher values of relative curvature are correlated with flatter surfaces. The spheres used in this test had a relative curvature K of about 1.0. The oblates had a relative curvature K of about 1.2, and the flat tablets had a relative curvature K of indefinite magnitude. One may conclude that a value for K between 1 and 1.2 is optimal.

In general, tablets with about 4% gelator seem to have a good resistance against fracture when being pushed through an aluminium foil. It was also found that the presence of at least 2 weight percent of a gel-forming gelatin (such as BS100) may lead to tablets with a very good score in a push through test. This may be due to a higher "network" degree in these tablets. Tablets having a non gel-forming gelatin (such as Sol P) as additional compound in the gelator are however preferred, due to better disintegration properties.

TABLE 8

| Sample | Gelatin Sol P (% w/v) | BS 100 (% w/v) | Mannitol (% w/v) | Shape | Percentage intact |
|---|---|---|---|---|---|
| 1 | 8 | 0 | 9 | oblate | 0 |
|   | 8 | 0 | 9 | sphere | 0 |
|   | 8 | 0 | 0 | tablet | 0 |
| 2 | 0 | 4 | 3 | oblate | 100 |
|   | 0 | 4 | 3 | sphere | 100 |
|   | 0 | 4 | 3 | tablet | 0 |
| 3 | 3 | 1 | 3 | oblate | 0 |
| 4 | 2 | 2 | 3 | oblate | 10 |
|   | 2 | 2 | 3 | sphere | 40 |
|   | 2 | 2 | 3 | tablet | 0 |
| 5 | 2 | 2 | 8 | oblate | 40 |
|   | 2 | 2 | 8 | sphere | 100 |
|   | 2 | 2 | 8 | tablet | 0 |
| 6 | 1 | 3 | 3 | oblate | 100 |
|   | 1 | 3 | 3 | sphere | 80 |
|   | 1 | 3 | 3 | tablet | 0 |
| 7 | 4 | 0 | 3 | oblate | 0 |
| Tablet |  | 4* | 3 | tablet | 0 |

*type of gelatin not known

The invention claimed is:

1. A process for the preparation of a fast-disintegrating tablet containing a medicinal substance, comprising the steps of:
    providing a fluid formulation comprising the medicinal substance,
    providing a solid element having formed therein at least one cavity,
    cooling the solid element to a temperature below a freezing temperature of the formulation,
    filling the cavity with the fluid formulation after said cooling,
    solidifying the formulation while present in the cavity to form a solid pellet comprising the medicinal substance without actively shaping the entire surface of the pellet, wherein the volume of the cavity is smaller than 50% of the volume of the pellet,
    taking the pellet out of the cavity, and
    drying the pellet in a vacuum to obtain the tablet.

2. A process according to claim 1, characterised in that the formulation is cooled by extracting heat from the formulation through a cavity wall by conduction.

3. A process according to claim 2, characterised in that the volume of the pellet is larger than a maximum volume of a free droplet of the fluid formulation at a temperature and pressure used when filling the cavity.

4. A process according to claim 3, characterised in that a speed at which the cavity is filled with the fluid formulation is chosen such that the surface of the part of the pellet that is in the cavity before the pellet is taken out of the cavity, is in essence a negative print of the surface of the cavity.

5. A process according to claim 3, characterised in that a cross-section of the part of the pellet that is in the cavity is smaller than a cross-section of the cavity at its entrance.

6. A process according to claim 5, characterised in that the volume of the cavity is smaller than the volume of the pellet.

7. A process according to claim 6, characterised in that a measure is taken to support automatic detachment of the pellet from the cavity wall.

8. A process according to claim 7, wherein the cavity is formed in a solid element characterised in that the automatic detachment is supported by keeping the temperature of the solid element adequately beneath the freezing temperature of the fluid formulation.

9. A process according to claim 8, characterised in that the pellet is taken out of the cavity by applying a pushing force to the pellet.

10. A process according to claim 9, characterised in that the pellet is pushed out of the cavity using a tangentially directed force.

11. A process according to claim 1, characterised in that multiple pellets are placed in a packed bed before the pellets are dried in the vacuum.

12. A process according to claim 11, characterised in that the pellets are packed in a heat conducting container having a bottom and side walls, and that a heat source is provided above a top layer of the packed pellets, the heat source having a surface directed to a top layer of the bed, which surface has an emissivity coefficient of at least 0.4, whereafter the pellets are subjected to the vacuum while at the same time heating at least the bottom of the container and the said surface to provide heat to the particles to support drying of the pellets.

* * * * *